United States Patent
Boutros (10) Patent No.: US 10,080,511 B1
(45) Date of Patent: Sep. 25, 2018

(54) BI-DIRECTIONAL OXYGENATION APPARATUS FOR A NON-INTUBATED PATIENT

(71) Applicant: Sean Boutros, Houston, TX (US)

(72) Inventor: Sean Boutros, Houston, TX (US)

( * ) Notice: Subject to any disclaimer, the term of this patent is extended or adjusted under 35 U.S.C. 154(b) by 0 days.

(21) Appl. No.: 15/672,530

(22) Filed: Aug. 9, 2017

(51) Int. Cl.
| | |
|---|---|
| *A61M 16/06* | (2006.01) |
| *A61B 5/08* | (2006.01) |
| *A61B 5/085* | (2006.01) |
| *A61B 5/091* | (2006.01) |
| *A61M 16/04* | (2006.01) |
| *A61M 5/172* | (2006.01) |

(52) U.S. Cl.
CPC .............. *A61B 5/085* (2013.01); *A61B 5/091* (2013.01); *A61M 16/06* (2013.01); *A61M 5/1723* (2013.01); *A61M 16/0488* (2013.01)

(58) Field of Classification Search
CPC .............. A41D 13/11; A61M 15/0016; A61M 15/0018; A61M 16/0048; A61M 16/047; A61M 16/10; A61M 16/208; A62B 23/00; A62B 23/02; A62B 7/00; A62B 7/10; A62B 9/06; B63C 11/18; B63C 11/205; B63C 11/22; B63C 9/00; B63C 9/1255
USPC ............ 128/200.14, 200.24, 201.11, 201.25, 128/201.26, 201.28, 202.14, 202.28, 128/202.29, 203.11, 203.12, 204.26, 128/205.13, 205.24, 205.27, 205.29, 128/206.11, 206.12, 206.15, 206.17, 128/207.12, 207.13, 207.1, 4, 207.16, 128/207.18, 207.29, 848, 859, 861, 863
See application file for complete search history.

(56) References Cited

U.S. PATENT DOCUMENTS

| | | | | |
|---|---|---|---|---|
| 4,304,229 A | * | 12/1981 | Curtin ................... | B63C 11/205 128/201.11 |
| 4,324,234 A | * | 4/1982 | Maness ................... | A62B 7/00 128/202.14 |
| 4,365,628 A | * | 12/1982 | Hodel ...................... | A62B 7/02 128/205.12 |
| 5,199,422 A | * | 4/1993 | Rasocha ................ | B63C 11/205 128/201.11 |
| 5,398,673 A | * | 3/1995 | Lambert ........... | A61M 16/0048 128/201.11 |
| 5,813,401 A | * | 9/1998 | Radcliff .............. | A61M 16/208 128/200.14 |
| 6,568,387 B2 | | 5/2003 | Davenport et al. | |
| 9,555,201 B2 | | 1/2017 | Collins et al. | |
| 2003/0140925 A1 | | 7/2003 | Sapienza et al. | |

(Continued)

*Primary Examiner* — Annette Dixon
(74) *Attorney, Agent, or Firm* — Dale J. Ream (57) ABSTRACT

A bi-directional oxygenation apparatus for a patient includes a mouthpiece including an intraoral portion for placement in the patient's mouth and defining a center orifice, the mouthpiece including an external portion coupled to the intraoral portion and in fluid communication with the center orifice. A valve port includes a continuous side wall operatively coupled to the external portion of the mouthpiece and defining an interior area in fluid communication with the center orifice, the valve port selectively moved toward or away from the external portion when air is inhaled or exhaled through the center orifice, respectively. A one-way positive-end expiratory pressure ("PEEP") valve is situated in the interior area of the valve port and configured to resist air exhaled by the patient through the center orifice.

14 Claims, 8 Drawing Sheets

(56) References Cited

U.S. PATENT DOCUMENTS

2007/0016105 A1* 1/2007 Mamourian .... A61M 25/09041
 600/585
2008/0257358 A1* 10/2008 Stern ...................... A61F 5/566
 128/207.16
2015/0258355 A1* 9/2015 Folkvord ............... A41D 13/11
 128/205.29

* cited by examiner

BI-DIRECTIONAL OXYGENATION APPARATUS FOR A NON-INTUBATED PATIENT

BACKGROUND OF THE INVENTION

This invention relates generally to medical equipment intended to increase oxygenation of the blood of a patient who has insufficient pressure in the lungs following exhalation.

Acute respiratory distress syndrome ("ARDS") is a lung condition that prevents enough oxygen from getting to the lungs and into the blood. This condition can be life-threatening if not treated appropriately and expeditiously. ARDS leads to a buildup of fluid in the air sacs (alveoli) of a lung which prevents enough oxygen from passing into the bloodstream. The fluid buildup also makes the lungs heavy and stiff, which decreases the lungs' ability to expand. The level of oxygen in the blood can stay dangerously low, even if the person receives oxygen from a breathing machine (ventilator) through a breathing tube (endotracheal tube). Blood and fresh inspired gas must be in close proximity to one another for gas change to occur A method to help prevent lung collapse (i.e. collapse of individual alveoli) at the end of expiration in critically ill mechanically ventilated patients is known as positive end-expiratory pressure (known as "PEEP"). Described briefly, PEEP refers to keeping a small amount of pressure in the lung at the end of expiration rather than letting the lung return to atmospheric pressure. The pressure remaining in the lung acts as a force pushing outward on the alveoli and holding them open to receive oxygen. In short, more oxygen is added to the blood, i.e. increased oxygenation of the blood. Traditionally, PEEP is a method provided mechanically by a ventilator in an intubated patient on a ventilator machine.

In a typical ventilation setup, a patient receives fresh oxygen or enhanced oxygenated air through tubes placed into his nostrils and into his lungs ("inhalation) while air is exhaled from his lungs into a ventilation machine through a tracheal tube. A one-way as positive end-expiratory pressure (PEEP) valve may be situated in the exhalation stream that provides mechanical resistance intended to increase the patient's lung pressure and, thereby, increasing the oxygenation of the patient's blood.

Although presumably effective for its intended use, the current method of treating a dangerously distressed patient with a full ventilator and intubated patient is undesirable for a patient that is not intubated and not being treated on a full ventilator setup. Stated another way, it would be desirable for a patient capable of inhaling and exhaling on his own to have a bi-directional oxygenation apparatus that allows the patient to inhale air through his mouth and then to exhale through his mouth with mechanical resistance being given to the exhalation, whereby to increase the pressure in the lung at the end of exhalation and, as a result, increase the oxygenation of his blood. In addition, it would be desirable to a bi-directional oxygenation apparatus having a mouthpiece and that is handheld.

SUMMARY OF THE INVENTION

A bi-directional oxygenation apparatus for a patient according to the present invention includes a mouthpiece including an intraoral portion for placement in the patient's mouth and defining a center orifice, the mouthpiece including an external portion coupled to the intraoral portion and in fluid communication with the center orifice. A valve port includes a continuous side wall operatively coupled to the external portion of the mouthpiece and defining an interior area in fluid communication with the center orifice, the valve port being selectively movable toward or away from the external portion of the mouthpiece when air is inhaled or exhaled through the center orifice, respectively. A one-way positive-end expiratory pressure ("PEEP") valve is situated in the interior area of the valve port and configured to resist air exhaled by the patient through the center orifice.

Therefore, a general object of this invention is to provide a bi-directional oxygenation apparatus for a patient that includes a mouthpiece that enables the patient to both inhale and exhale air through his mouth.

Another object of this invention is to provide a bi-directional oxygenation apparatus, as aforesaid, that includes a one-way PEEP valve that provides resistances to exhaled air so as to expand the patient's lungs and increase oxygenation of the patient's blood.

Still another object of this invention is to provide a bi-directional oxygenation apparatus, as aforesaid, in which the PEEP valve allows inhaled air to pass without resistance.

Yet another object of this invention is to provide a bi-directional oxygenation apparatus, as aforesaid, having a valve port operatively coupled to the mouthpiece and that is selectively movable toward or away from the mouthpiece when air is inhaled or exhaled, respectively.

A further object of this invention is to provide a bi-directional oxygenation apparatus, as aforesaid, in which the valve port is coupled to the mouthpiece with an elastic element naturally biased toward the mouthpiece.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2a is a front view of the bi-directional oxygenation apparatus as in FIG. 1a;

FIG. 2c is a sectional view taken along line 2c-2c of FIG. 2a;

FIG. 2e is a sectional view taken along line 2e-2e of FIG. 2a;

FIG. 3a is a top view of the bi-directional oxygenation apparatus of FIG. 1a;

FIG. 3b is a sectional view taken along line 3b-3b of FIG. 3a;

FIG. 4a is an exploded view of the bi-directional oxygenation apparatus as in FIG. 1a.

DESCRIPTION OF THE PREFERRED EMBODIMENT

A bi-directional oxygenation apparatus for a patient according to a preferred embodiment will now be described with reference to FIGS. 1a to 4b of the accompanying drawings. It will be understood that for the sake of convenience but stated here for clarity, the "bi-directional oxygenation apparatus 10" may correctly be referred to herein as an "oxygenation apparatus." The bi-directional oxygenation apparatus 10 includes a mouthpiece 20, a one-way PEEP valve 30, a collar member 40, a valve port 50, and an elastic member 60 for urging the valve port 50 toward the mouthpiece 20. It is understood that references herein to a patient refer to a patient who is not intubated or being treated on a complete respiratory system that essentially inhales and exhales for the patient. Rather, the present invention is for use by a non-intubated patient who is able to inhale and exhale on his own and through his while yet being in need of improved and increased oxygenation of his blood.

Figure 1A:
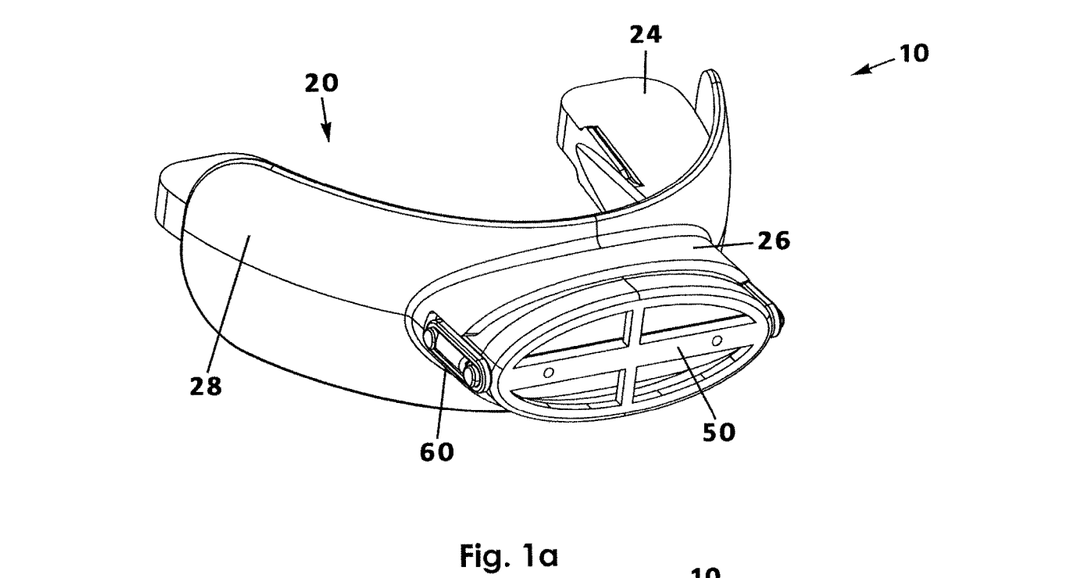
FIG. 1a is a perspective view of a bi-directional oxygenation apparatus according to a preferred embodiment of the present invention.
Figure 1B:
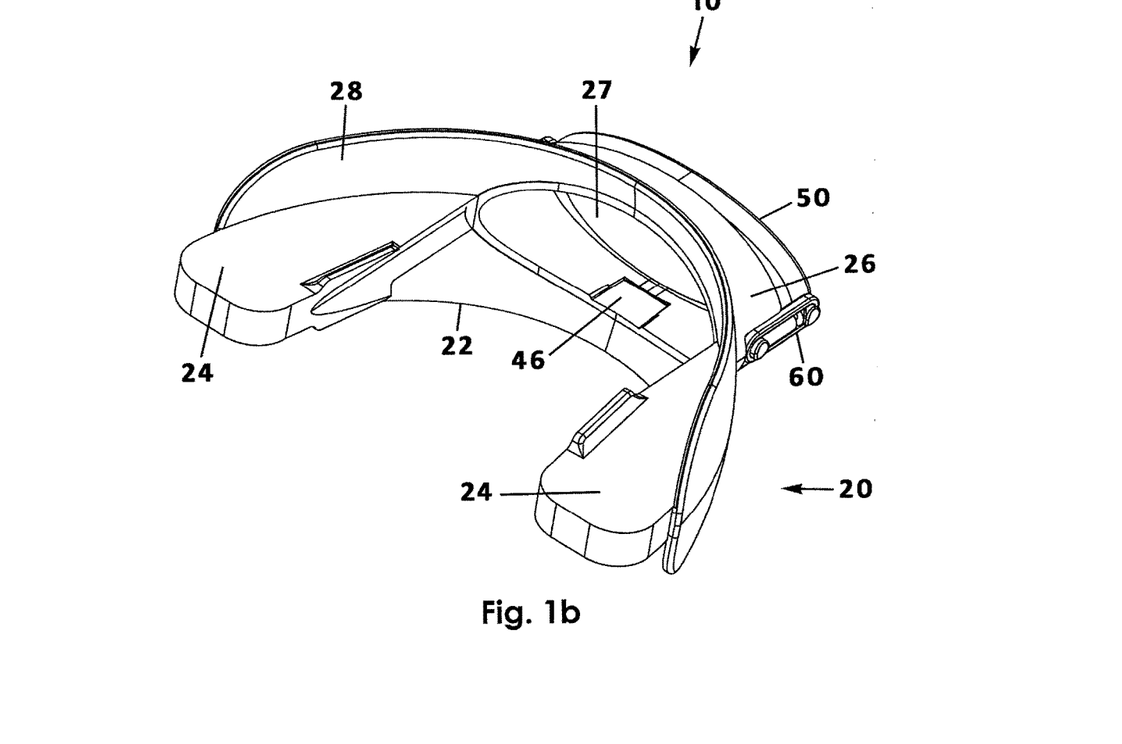
FIG. 1b is the perspective view of a bi-directional oxygenation apparatus as in FIG. 1 taken from a reverse angle.

The bi-directional oxygenation apparatus 10 includes a mouthpiece 20 that includes an intraoral portion 22 configured for placement inside a patient's mouth and an external portion 26 coupled to the intraoral portion 22 and configured to remain outside the patient's mouthpiece. In its simplest form, the intraoral portion 22 has structures similar to those of a football mouthpiece that may be gripped in between the teeth of a football player. For instance, the mouthpiece 20 may include left and right grip members 24 spaced apart laterally within a horizontal plane or arranged in a bowed configuration complementary to the bowed configuration of a patient's teeth so as to be gripped by the patient's teeth during use (FIG. 1b).

Further, the mouthpiece 20 includes a mouth shield 28 that is positioned intermediate the intraoral portion and the external portion 26. The mouth shield 28 may have a generally hemispherical shape configuration and be both configured and positioned to press against the lips and cheeks of the patient when the intraoral portion 22 is taken into the patient's mouth. The external portion 26 of the mouthpiece 20 defines a central orifice 27 through which air may be inhaled and exhaled by a patient as will be described in further detail below. It may be seen that the intraoral portion 22 and external portion 26 define the central orifice 27 in combination or in communication with one another (FIG. 1b).

The valve port 50 is the outermost component of the oxygenation apparatus 10 and is the component that is moved toward or away from the mouthpiece as air is inhaled or exhaled, respectively. The valve port 50 is operatively connected to the mouthpiece 20 in a manner that allows in and out movement relative to the mouthpiece 20 although it is understood that additional structures may be positioned intermediate the valve port 50 and external portion 26 of the mouthpiece 20 as will be described below. The valve port 50 includes a continuous side wall 52 that defines an interior area in fluid communication with the central orifice 27 defined by the mouthpiece 20. The valve port 50 may include an end shield 54 configured to partially block access to the interior space while still allowing inhalation or exhalation of air therethrough as will be described in more detail below. The end shield 54 may be configured as a grate having one or more support members arranged in a crisscross pattern.

The valve port 50 is normally biased to move toward contact with or connection to the mouthpiece 20 by at least one elastic member 60 extending between the valve port 50 and external portion 26 of the mouthpiece 20. In an embodiment, the elastic member 60 may be a rubber band normally biased to tighten the components together to which ends of the rubber band is attached—in this case to flanges or posts positioned on respective components. It is understood that the elastic member 60 has the characteristic of being lengthened or stretched when the valve port 50 is moved away from the mouthpiece 20 and is resilient to return to an original and predetermined length and tension when the valve port 50 is moved toward the mouthpiece 20. Further, it is understood that the spring-like tension of the elastic member 60 increases as it is stretched or expanded and, conversely, is reduced or loosened when the elastic member 60 is moved or tightened toward the external portion 26 of the mouthpiece 20.

In an embodiment of the present invention, a collar member 40 is situated intermediate the valve port 50 and the mouthpiece 20 and provides the structures that make the invention operate efficiently. Specifically, the collar member 40 may have a continuous side wall arranged in an oval shaped configuration although a combination of walls arranged in a rectangular, circular, or irregular configuration would also work. The continuous side wall of the collar member 40 defines a hollow interior space open on both front and rear ends in communication with the central orifice 27 of the mouthpiece 20 and with the open interior area of the valve port 50. In other words, the collar member 40 is essentially a pass through fitting through which ambient or processed air is inhaled by the patient and through which air from the patient's lungs is exhaled.

The collar member 40 may have a diameter slightly smaller than a diameter of the central orifice 27 of the external portion 26 of the mouthpiece 20 so as to be received therein in a tight friction fit arrangement. The external portion 26 may define one or more slots (not numbered) for receiving components attached to the collar member 40 as will be described later. In embodiments not shown, the collar member 40 may have a unitary construction with the external portion 26 of the mouthpiece 20 such that the valve port 50 is actually connected directly to the mouthpiece 20.

The collar member 40 may be coupled to the valve port 50 with one or more elastic members 60 so as to naturally urge these components toward one another while still allowing the vale port 50 to move away therefrom under tension. More particularly, at least one first flange 56 (also known as a "first post") may be coupled to an exterior surface of the valve port 50 although the first flange 56 may be mounted to an internal or other surface of the valve port 50 in some embodiments. Similarly, at least a second flange 42 (also known as a "second post") may be coupled to an external surface of the collar member 40, again it being understood that the second flange 42 may be mounted to an internal or other surface of the collar member 40 in some embodiments. Preferably, the first flange 56 is actually manifested as a pair of first flanges with each first flange 56 being spaced apart and separated from its counterpart and positioned, for instance, at ends of the valve port 50 as shown in the accompanying drawings. Similarly, the second flange 42 may be actually manifested as a pair of second flanges with each second flange 42 being spaced apart and separated from its counterpart and positioned, for instance, at ends of the collar member 40 as shown in the accompanying drawings.

The elastic member 60 is a loop of resilient material such as rubber. The elastic member 60 may be coupled to respective first and second flanges in a tightening, biased relationship. More particularly, the elastic member 60 may be a rubber band having a predetermined amount of tension coupled to respective flanges for normally urging the valve port 50 to bear against the collar member 40. In some embodiments, a gasket or o-ring seal may be sandwiched between the collar member 40 and valve port 50 or other components so as to seal against air leakage in use. In other embodiments (not shown), the elastic member 60 may utilize other types of resistive or tension technology, such as an air piston/cylinder combination that provides a predetermined amount of tension.

In addition, a guide assembly is provided to maintain smooth and efficient movement of the valve port 50 relative to the mouthpiece 20. In other words, in and out movement is made smooth and effected by the mere inhalation or exhalation of air by a patient. More particularly, at least one receiving member 70 (and preferably a pair of receiving members) is mounted to an exterior surface of the collar member 40, the receiving member 70 having a generally tubular configuration that defines a channel 72 having a linear configuration and defining an internal diameter. The guide assembly also includes a guide rod 74 (and preferably a pair of spaced apart guide rods) coupled to an exterior surface of the valve port 50 and oriented to extend in the direction of the mouthpiece 20. The receiving member 70 of a respective guide assembly defines a channel 72 configured to receive a respective guide rod 74 therein and allows relative back and forth (i.e. in and out) movement as the valve port 50 is moved toward or away from the mouthpiece 20 as described above. The guide rod 74 may be situated adjacent the first flange 56 of the valve port 50 while the receiving member 70 may be situated adjacent the second flange 42 although internal or other configurations may be chosen. The receiving member 70 may be received in the slots defined by the external portion 26 of the mouthpiece 20 described above.

Figure 2A:
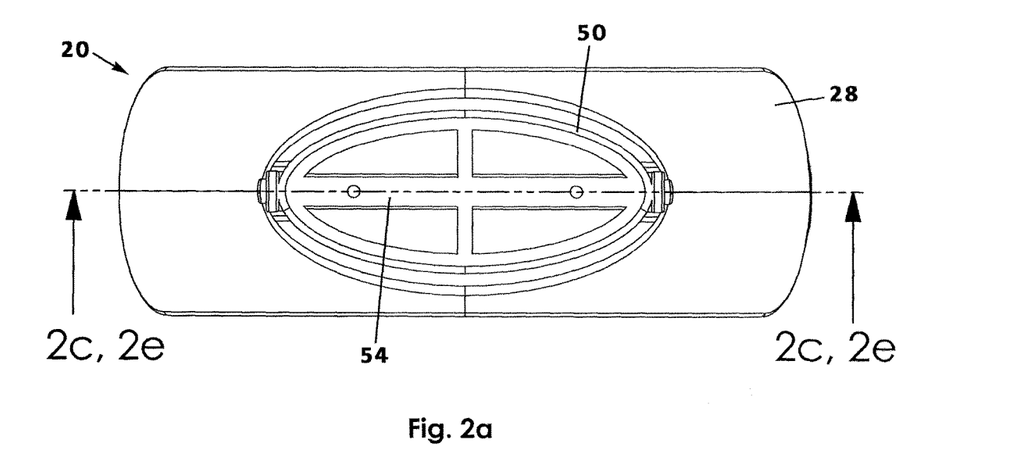
Figure 2B:
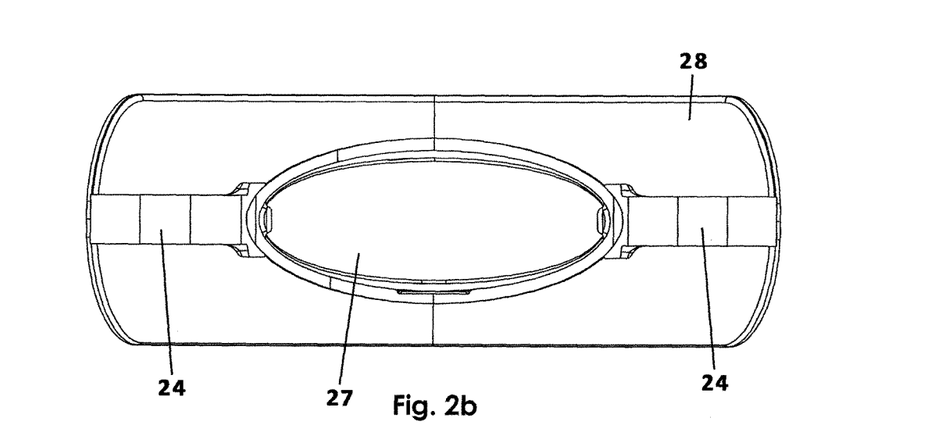
FIG. 2b is a rear view of the bi-directional oxygenation apparatus as in FIG. 1b.
Figure 2C:
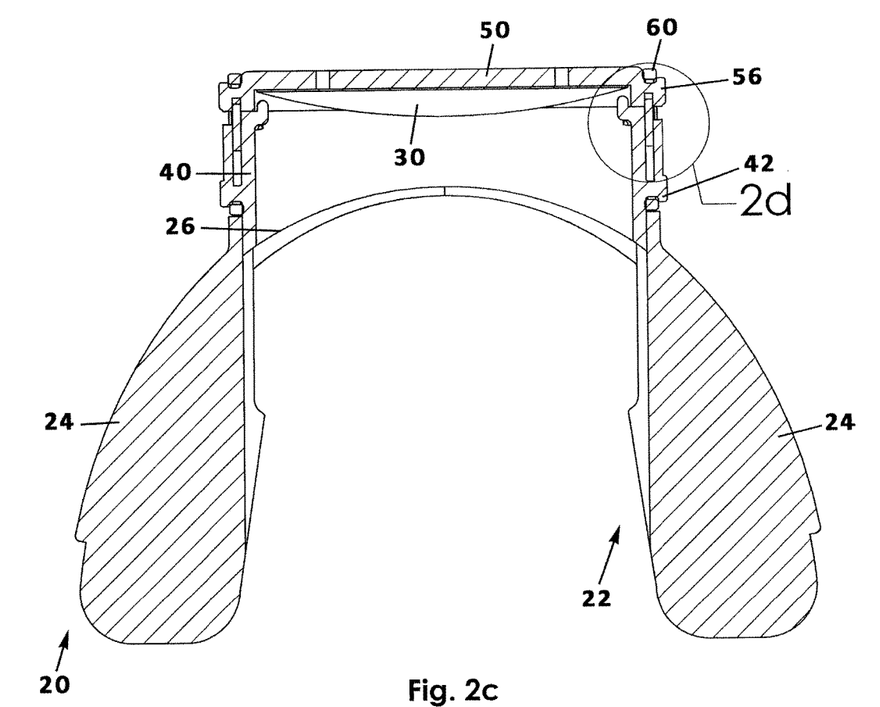
Figure 2D:
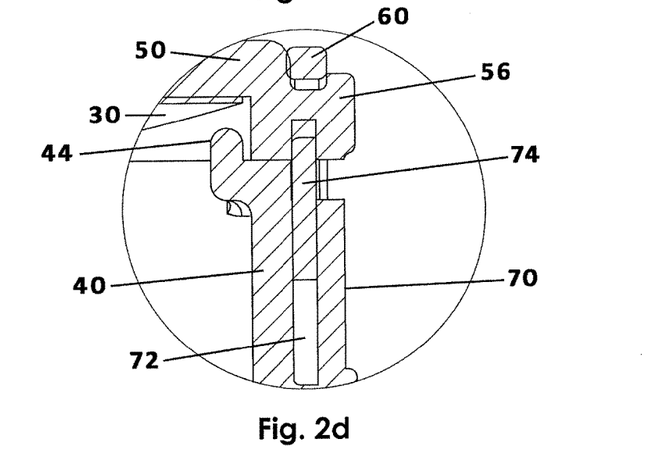
FIG. 2d is an isolated view on an enlarged basis taken from FIG. 2c.
Figure 2E:
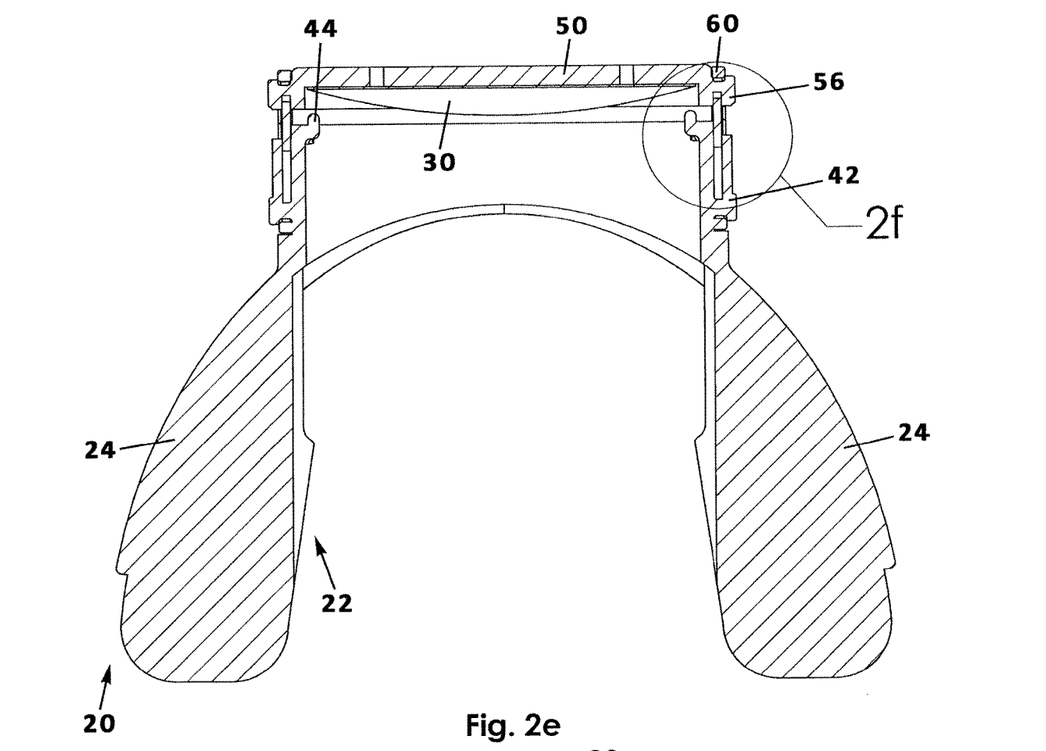
Figure 2F:
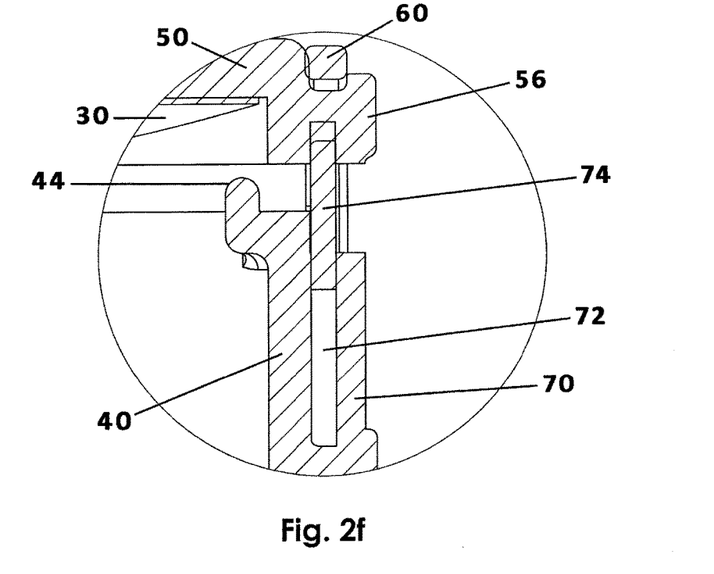
FIG. 2f is an isolated view on an enlarged basis taken from FIG. 2e.
Figure 3A:
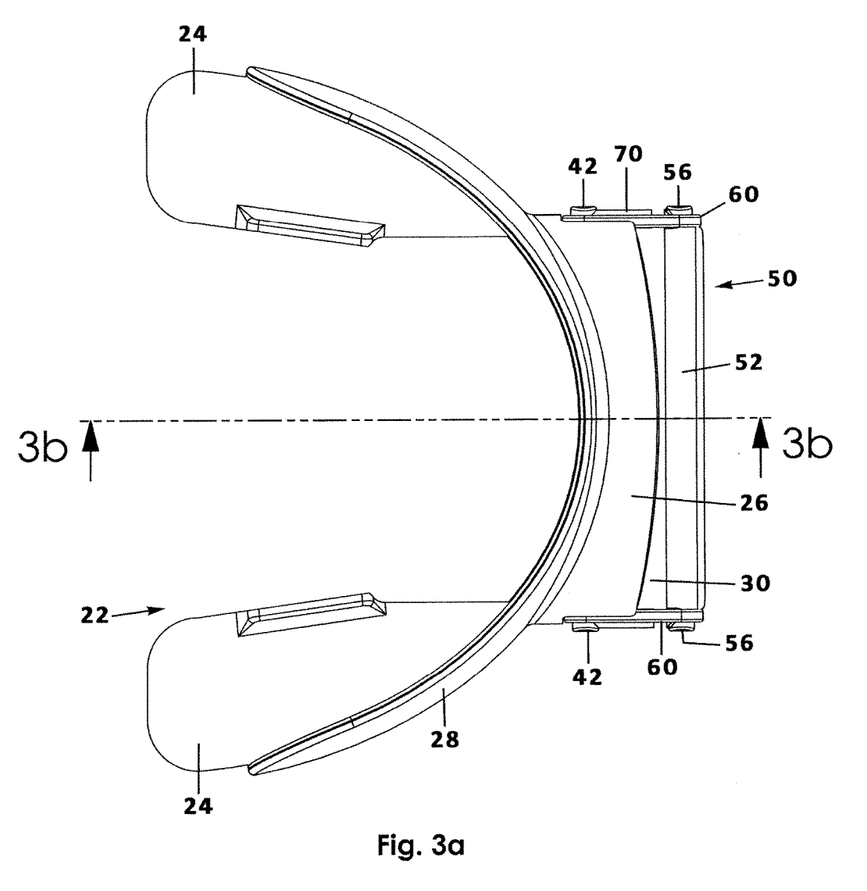
Figure 3B:
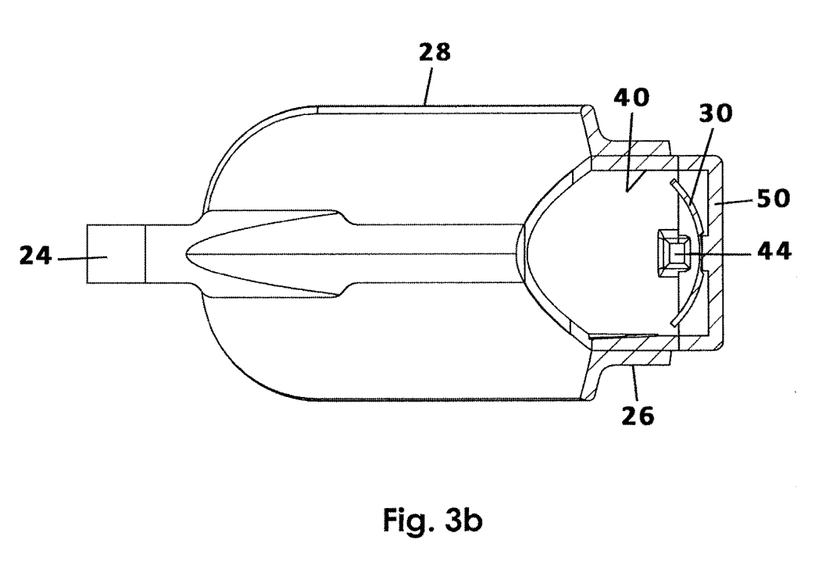
Figure 4A:
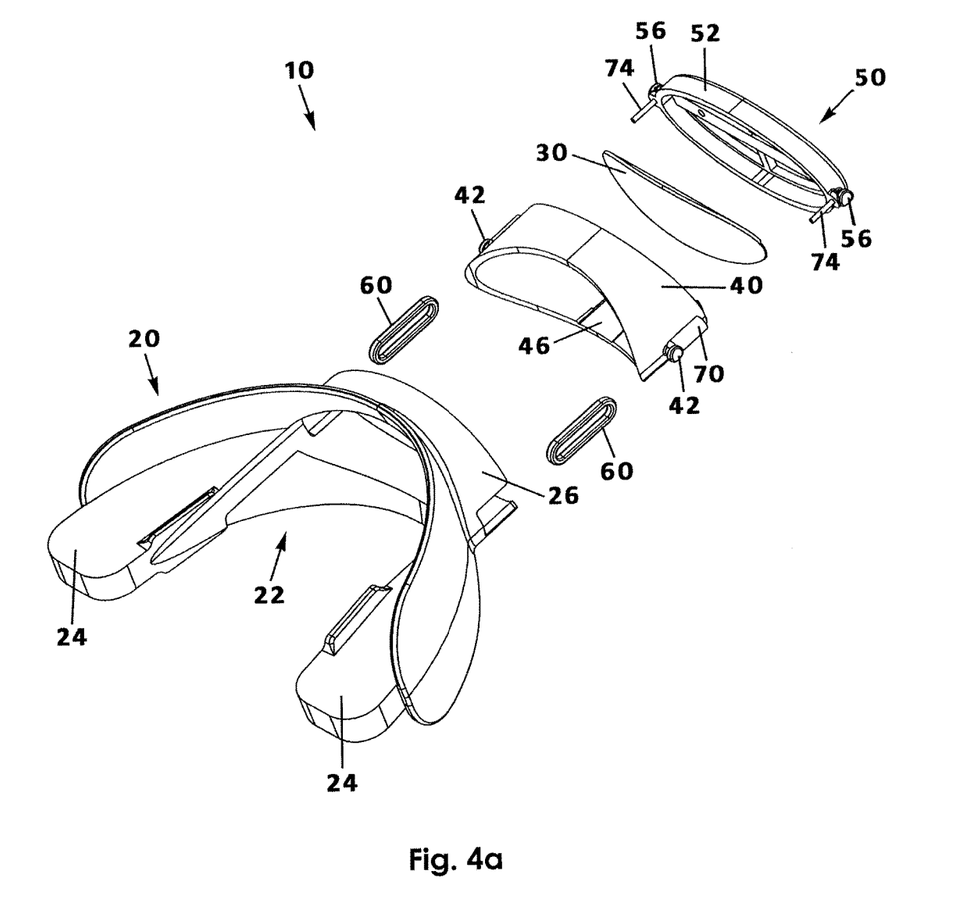
Figure 4B:
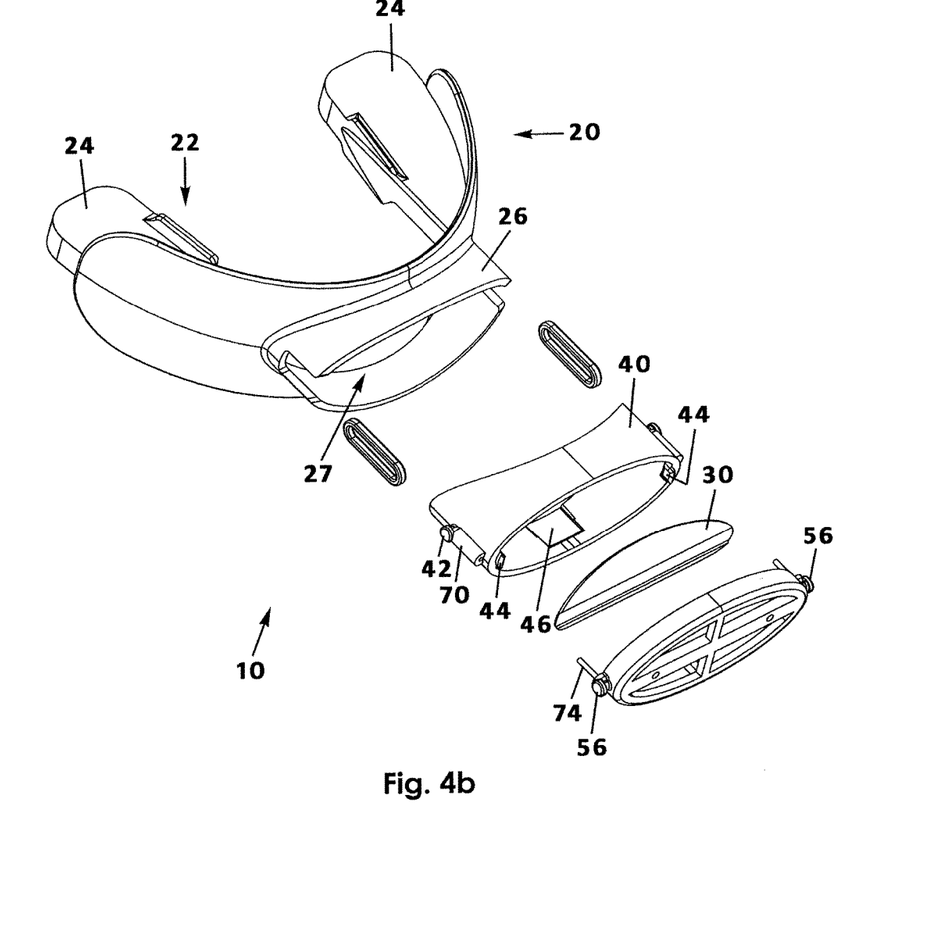
FIG. 4b is an exploded view of the bi-directional oxygenation apparatus as in FIG. 1b.

In an important aspect, the one-way PEEP valve 30 is positioned intermediate the mouthpiece 20 and valve port 50 and configured to allow inhaled air to pass without resistance while providing a predetermined amount of resistance to air being exhaled from a patient's lung through the bi-directional oxygenation apparatus 10 as described above. The PEEP valve 30 may be constructed of silicone and situated to span the open interior space defined by the collar member 40 such that all inhaled and exhaled air passes through the PEEP valve 30. In an embodiment, the collar member 40 may include one or more mounting flanges 44 by which ends of the PEEP valve 30 are mounted therein (FIG. 4*b*). The PEEP valve 30 has a flexible construction and is mounted inside the collar member 40 so as to bow outwardly away from the mouthpiece 20 and toward the valve port 50 when air is exhaled through the central orifice 27. In other words, the PEEP valve 30 has a convex configuration when viewed from the mouthpiece 20 (FIG. 2*c*).

In another aspect, a lower or bottom interior surface of the collar member 40 may be recessed to define a collection area 46 (FIG. 1*b*). More particularly, the collection area 46 is configured to collect saliva that may come through the central orifice 27 as part of the air exhaled by a patient. The collection area 46 may include a rearwardly and downwardly angled surface such that collected saliva is returned to the mouthpiece and, ultimately, to the mouth of the patient. This structure is important so that moisture is not accumulated on the surface of the silicon PEEP valve 30.

In use, a non-intubated patient in need of enhancing the oxygenation of his blood by expansion of his lung capacity can inhale and exhale through the football style mouthpiece 20 of the bi-directional oxygenation apparatus 10 as described above. Ambient air may be inhaled through the mouth and without any resistance. Then, the inhaled air may be exhaled through the mouthpiece, the exhaled air passing through a one-way peep valve 30 which provides mechanical resistance as described above. The resistance may be provided by one or more rubber bands that are normally biased to resist outward movement of a valve port being urged outwardly by the outward bowing of the flexible peep valve itself. With each cycle of inhalation and then exhalation, the lungs of the patient are expanded, more oxygen is retained at the conclusion of an exhalation and, as a result, more oxygen is received into the blood (i.e. oxygenation occurs).

Accordingly, the present invention allows peep therapy to be available to a non-intubated patient in need of enhanced oxygenation during an exhalation of air from his lungs.

It is understood that while certain forms of this invention have been illustrated and described, it is not limited thereto except insofar as such limitations are included in the following claims and allowable functional equivalents thereof.

The invention claimed is:

1. A self-administered oxygenation apparatus configured to increase pressure within a non-intubated patient's lungs and thereby configured to increase an amount of oxygen in the non-intubated patient's blood when operated solely by the non-intubated patient who is capable of unassisted inhalation and exhalation, said self-administered oxygenation apparatus comprising:
    a mouthpiece having an external portion defining a center orifice through which the patient selectively inhales and exhales air from his lungs;
    a valve port having a continuous side wall operatively coupled to said external portion of said mouthpiece and defining an interior area in fluid communication with said center orifice, said valve port being selectively moved toward or away from said external portion when air is inhaled or exhaled through said center orifice, respectively;
    a collar fixedly attached to said exterior portion of said mouthpiece that defines a hollow interior space in fluid communication with said central orifice and with said interior area of said valve port;
    a first flange coupled to an external surface of said continuous side wall of said valve port;
    a second flange coupled to an external surface of said collar, said second flange being displaced from said first flange;
    an elastic member having a loop of resilient material coupled to said first flange and to said second flange in a tightening, biased relationship for operatively coupling said valve port to said mouthpiece, said elastic member continuously biasing said valve port toward said external portion of said mouthpiece;
    wherein said first flange, said second flange, and said elastic member are external of said collar and are exposed;
    a one-way positive-end expiratory pressure ("PEEP") valve positioned intermediate said interior area of said valve port and said mouthpiece, said PEEP valve being configured to resist air exhaled by the patient through said center orifice;
    wherein said collar member is a pass through fitting configured such that ambient or processed air is inhaled by the patient and through which air from the patient's lungs is exhaled.

2. The self-administered oxygenation apparatus as in claim 1, wherein said elastic member is a rubber band that selectively expands in length when said valve port is moved away from said mouthpiece and is resilient to return to an original length when said valve port is moved toward said mouthpiece.

3. The self-administered oxygenation apparatus as in claim 1, wherein:

said first flange is a pair of first flanges spaced apart from one another on said exterior surface of said valve port;
said second flange is a pair of second flanges spaced apart from one another on said collar.

4. The self-administered oxygenation apparatus as in claim 1, wherein said one-way PEEP valve is constructed of silicone configured to allow the inhaled air to pass without resistance.

5. The self-administered oxygenation apparatus as in claim 1, wherein said one-way PEEP valve has a flexible construction that bows away from said mouthpiece when impacted by air exhaled by the patient through said central orifice so as to urge said valve port to move away from said mouthpiece.

6. The self-administered oxygenation apparatus as in claim 1, wherein said mouthpiece includes an intraoral portion for placement in the patient's mouth, said intraoral portion being coupled to said external portion and in fluid communication with said center orifice.

7. The self-administered oxygenation apparatus as in claim 6, wherein:
said intraoral portion of said mouthpiece includes left and right grip members arranged in a bowed configuration and configured for insertion between teeth of the patient;
said mouthpiece includes a mouth shield intermediate said intraoral portion and said external portion, said mouth shield having a hemispherical shape configuration.

8. The self-administered oxygenation apparatus as in claim 1, wherein said valve port includes an end shield partially blocking access to said interior area thereof but allowing air to be inhaled or exhaled therethrough.

9. The self-administered oxygenation apparatus as in claim 1, further comprising a seal ring coupled to one of said collar, said exterior portion of said mouthpiece, or said valve port and configured to seal against air leakage.

10. The self-administered oxygenation apparatus as in claim 1, wherein said PEEP valve is mounted to an internal surface of collar and positioned to span the interior space thereof so that air exhaled by the patient passes through said PEEP valve.

11. The self-administered oxygenation apparatus as in claim 1, wherein an interior surface of said collar defines a collection area that is configured to collect saliva that passes through said central orifice.

12. The self-administered oxygenation apparatus as in claim 11, wherein said collection area has a downwardly angled surface in a direction toward said mouthpiece so as to return collected saliva thereto.

13. The self-administered oxygenation apparatus as in claim 1, further comprising a guide assembly having a receiving member coupled to said collar that defines a channel and a guide rod coupled to said valve port, aid said channel configured to receive said guide rod in relative in/out movement as said valve port is moved toward or away from said mouthpiece, respectively.

14. The self-administered oxygenation apparatus as in claim 1, wherein said elastic member is lengthened by and a space is created between said first flange of said valve port and said second flange of said collar member when the air inhaled by a patient is exhaled from the patient's lungs, said inhaled air being exhaled from the patient's lungs through said space.

* * * * *